United States Patent [19]

Welt

[11] Patent Number: 4,624,259
[45] Date of Patent: Nov. 25, 1986

[54] FULL BODY TANNING APPARATUS

[76] Inventor: Glenn Welt, 1117 Perimeter Cir. West, Suite N122, Atlanta, Ga. 30346

[21] Appl. No.: 689,912

[22] Filed: Jan. 9, 1985

[51] Int. Cl.$^4$ .............................................. A61N 5/06
[52] U.S. Cl. .................................... 128/396; 362/220; 362/427
[58] Field of Search ................. 128/395, 396; 362/217, 362/220, 225, 230, 413, 414, 418, 419, 427, 428, 429, 430, 435; 248/129, 130, 425

[56] References Cited

U.S. PATENT DOCUMENTS 2,352,496  6/1944  Rose ............................... 362/427 X

FOREIGN PATENT DOCUMENTS

| 106395 | 4/1984 | European Pat. Off. ............ 128/395 |
| 2827802 | 1/1980 | Fed. Rep. of Germany ...... 128/396 |
| 460583 | 12/1950 | Italy ..................................... 128/396 |
| 2082747 | 3/1982 | United Kingdom ................ 128/396 |

Primary Examiner—Anton O. Oechsle
Attorney, Agent, or Firm—Harry W. Barron

[57] ABSTRACT

Described herein is a tanning system consisting of a six-foot high canopy containing six UVA radiation emitting bulbs. The canopy is attached to a frame in a rotational manner, allowing it to rotate from the vertical to the horizontal direction over a ninety degree arc. The frame is coupled to a base which includes a pair of casters and three ballast units causing the base to contain the majority of the weight of the entire unit while comprising only a small percent of the total volumn of the system. The type of bulbs are specially designed to emit approximately one tenth of one percent UVB radiation, which is the type which causes sunburn. Also included in the base is a 30-minute timer which allows the bulbs to be turned on for a maximum of thirty minutes. The canopy itself is constructed of molded ⅛" thick ABS material. The bulbs are held by bulb holders and the canopy material extends over the bulbs to prevent them from falling out if the become disengaged from the bulb holders.

24 Claims, 7 Drawing Figures

FULL BODY TANNING APPARATUS

This invention relates to tanning apparatus, and more particularly to portable tanning apparatus capable of tanning the entire body of a person.

During every summer thousands of people avail themselves of the warm rays of the sum to achieve a suntanned look. Tanning occurs by certain wavelengths of ultraviolet light naturally emitted by the sun. The tanning ultraviolet light is generally found in the wavelength of 315 to 380 nanometers and is conventionally called UVA light. Other types of ultraviolet light such as UVB light having a wavelength between 280 and 315 nanometers or UVC light, having a wavelength between 180 and 200 nanometers can cause severe sunburn to the person tanning themselves.

During the winter, particularly in colder areas, it is not practical to obtain a suntan from the sun. To allow people to tan themselves during the colder months, artificial tanning devices have been manufactured and sold for many years. Typically, those devices are small and can only be used to tan a portion of the user's body at any instant of time. Thus, to tan the entire body, several sittings are required. These prior art devices typically put out a combination of both UVA and UVB light and therefore have strict limits as to the amount of time a person can be exposed to the rays. For example, a typical ultraviolet lamp provides approximately five percent or more UVB radiation. Generally, safety requires that a person only use such a tanning device for approximately ten minutes at a time.

Recent developments have provided a state of the art tanning lamp which provides approximately 1/10th of one percent of UVB radiation. Obviously, this lamp is considerably safer than the prior lamps. As example of such a lamp is the 100W/10R UVA lamp manufactured and sold by Philips NV of the Netherlands. This lamp, in addition to providing a very small amount of the dangerous UVB radiation, also includes its own internal reflector, and operates at a low temperature. The lamp also is shaped like a conventional fluorescent bulb and may, for instance, be six feet in length.

In order to take advantage of the new UVA lamp, one can design a tanning device which is of a sufficient length to provide even radiation to the entire body of a user. Because of the low heat generated and the internal reflector, one can further take advantage of these lamps by designing a device which does not have built-in reflectors or fans to remove the heat. Such a device would be considerably lighter than any prior art tanning devices, and acordingly is adaptable to being portable.

In accordance with one aspect of this invention there is provided a portable tanning system for providing tanning radiation towards a user comprising a canopy for holding a plurality of bulbs of a type providing ultraviolet light with less than one percent of the ultraviolet light having a wavelength less than 315 nanometers. The canopy has a wire receptacle and path therein for coupling the received wires to the bulbs. The canopy further has an open front and a heat pervious material covering the back. The system additionally has a base including at least one ballast for the bulbs and means to connect the ballast to a source of household current. The base also has a wire outlet. The system further has connecting means of hollow lightweight material for connecting the canopy wire receptacle to the base wire outlet and for holding the canopy in a position to provide the tanning rays towards the user.

One preferred embodiment of the subject invention is hereafter described with specific reference being made to the following figures, in which.

Figure 1:
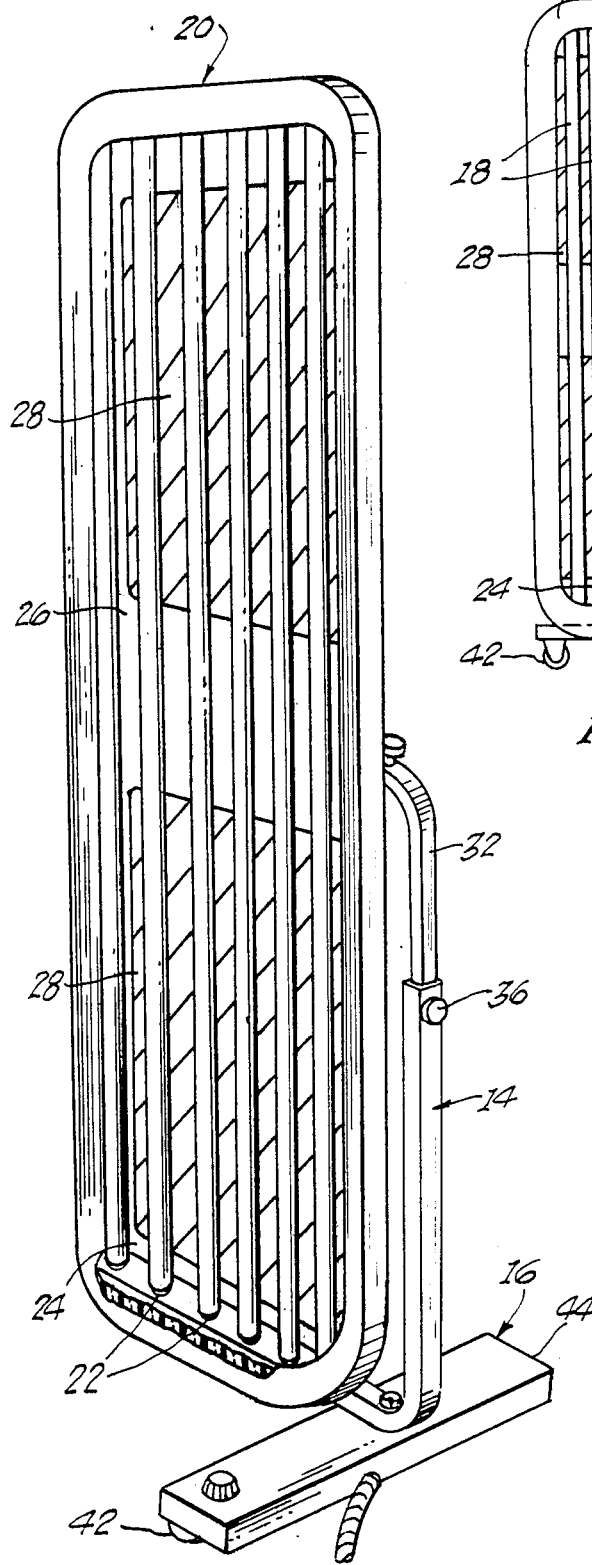
FIG. 1 is a perspective view of the tanning system of the subject invention.

Referring now to FIGS. 1 through 4, tanning system 10 is shown which includes a canopy 12, a frame 14, and a base 16. Frame 14 is coupled to both canopy 12 and base 16. Within canopy 12 are six UVA six-foot bulbs 18, which may be, for instance, Philips 100 W/10R R-UVA bulbs manufactured and sold by Philips NV of the Netherlands. These bulbs provide less than one percent UVB light and in fact approximately one tenth percent UVB light. The six bulbs 18 fit within canopy frame 20 and are held by bulb holders 22 positioned at the top and bottom of canopy frame 20. Canopy frame 20 may be fabricated of a molded plastic, such as one eighth inch thick ABS and has front extension 24 about the circumference of the front surface. Extensions 24 extending over bulb holders 22 prevent bulbs 18 from falling out if they become disconnected from bulb holders 22. The extensions 24 and thickness of canopy frame 20 also maintain bulbs 18 within the outside plane of frame 20 so that they do not extend out of frame 20. This prevents damage to the bulbs as well as preventing them from falling from canopy 12.

Behind bulbs 18 is a brace 26 which maintains rigidity in canopy 12 and is used to rotate canopy 12. Coupled from the top to the bottom of canopy 12 is a heat pervious cloth material 28. Because of the internal reflectors within bulbs 18, it is unnecessary to provide a reflective surface behind the bulbs, as in conventional tanning devices. This eliminates much of the heat generated by the bulbs towards the back of canopy 12. Accordingly, any lightweight backing may be used, such as cloth material 28. Furthermore, no fans are required to dissipate heat. Constructed in the manner described herein canopy 12 including the six bulbs 18, becomes very light in weight.

Figures 2, 3, 4:
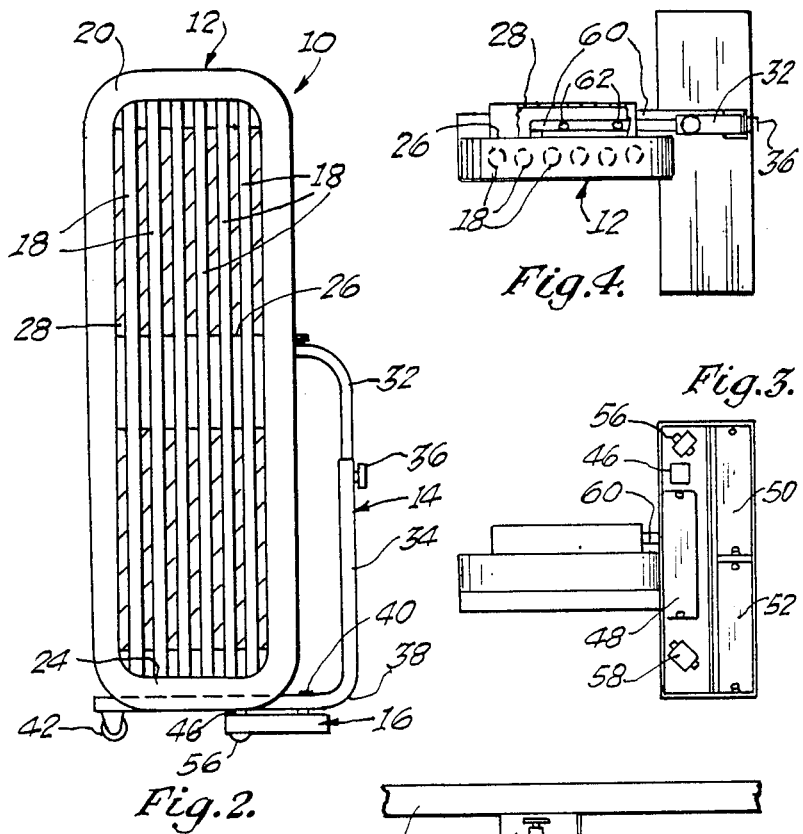
FIG. 2 is a front view of the system shown in FIG. 1.
FIG. 3 is a view of the bottom of the base of the tanning system shown in FIG. 1.
FIG. 4 is a top view of the canopy portion of the system shown in FIG. 1.

Canopy 12 is connected to frame 14 from the back thereof, as best seen in FIG. 4. Canopy 12 is free to rotate from the vertical position, as shown, to a horizontal position in which the bulbs 18 are pointed downward. This allows a person to use tanning system 10 while standing or seated in a chair when it is in a position as shown in FIG. 1 or while laying down when canopy 12 is rotated 90 degrees to the horizontal position. Lock 30 is used to secure canopy 12 in the desired rotational position. Lock 30 may have a triangular shaped knob to allow a better grip so that it can be easily turned to securely fasten canopy 12 in the desired rotational position.

Frame 14 consists of two parts, an upper part 32 and a lower part 34, with upper part 32 fitting inside lower part 34. Constructed in this manner upper part 32 may be raised or lowered within lower part 34 and secured by lock 36. Lock 36 may be a spring loaded member which is pulled to allow upper part 32 to be raised to the desired amount. Lock 36 is then released and may fit within a hole within upper part 34. Upper part 32 of frame may be constructed of 1¼" thick square hollow aluminum material and lower part 34 may be constructed of 1½" square hollow aluminum material. Lower part 34 is bent and secured to base 16 right near the curve 38 by securing bolt 40.

As seen in FIG. 2, the bottom portion of lower part 34 extends the length of canopy 12 and has a caster 42 at the end thereof. The length in which caster 42 is positioned away from the edge of lower part 34 of frame 14 is designed so that when frame 14 rotates about bolt 40 caster 42 fits adjacent to the side 44 of base 16. This allows tanning system 10 to become compacted for easy storage. The tanning system is considered to be in its operating position when frame 14 is positioned relative to base 16 as shown in FIG. 2, in which position the base is considered to be vertically disposed. In the FIG. 2 position of frame 14, caster 42, and casters 54 and 56 in the base triangularly support the system.

Base 16 includes a timer 46 which can be set to turn on or turn off the power to bulbs 18. Because of the low amount of UVB radiation emitted by bulbs, timer 46 can be set up to thirty minutes. Within base 46 are three ballasts 48, 50 and 52 and two casters 54 and 56. As can be seen in FIGS. 2 and 3, casters 54 and 56 are offset with respect to the longitudinal axis of the base. Thus, when tanning system 10 is in its compacted condition, i.e., with caster 42 adjacent side 44 of base 16, the offset nature of casters 54 and 56 allows the base to assume a freestanding position wherein its is disposed at an angle other than vertical with respect to the ground. These are positioned as seen in FIG. 3. Each of the ballasts 48, 50 and 52 control a pair of bulbs 18. The wires from ballasts 48, 50 and 52 and timer 46 are applied through bolt 40 which may be a hollow bolt and into hollow frame 14. The wires are applied through frame 46 into canopy 12. Power is applied to ballasts 48, 50 and 52 over cord 58 from ordinary household current.

Referring now to FIG. 4, a top view of system 10 is shown. Specifically it is shown how canopy 12 is coupled to the upper portion 32 of frame 14. An internal pipe 60 behind canopy 12 fits into upper portion 32 of frame 14 so that it can rotate therein. Bolts 62 hold upper portion 32 to canopy 12. The wires from base 16 which extend through frame 14 extend through pipe 60 and the interior sides of canopy 14 to the bulb holders 22 which are positioned at the top and bottom of canopy 14.

Connected in the manner described above, the majority of the weight of system 10 is contained in base 14. This is because the three ballasts 48, 50 and 52 are contained in base 14. Because of this the center of gravity of tanning system 10 is low causing system 10 to be stable when used. For example, the entire canopy 12 may weight in the neighborhood of twelve pounds, while the entire unit weighs 41 pounds. Thus, it is seen that less than 30 percent of the weight is within the canopy and over seventy percent of the weight is in the frame 14 and base 16 portions. At the same time, the frame 14 and base 16 portions only constitute a small percentage of the total volume. Because the frame 14 is made of lightweight structural aluminum the vast majority of the weight is concentrated in the base 16. This concentration of weight in base 16 makes it difficult to tip over tanning system 12 if it is accidentally bumped into.

Figure 5C:
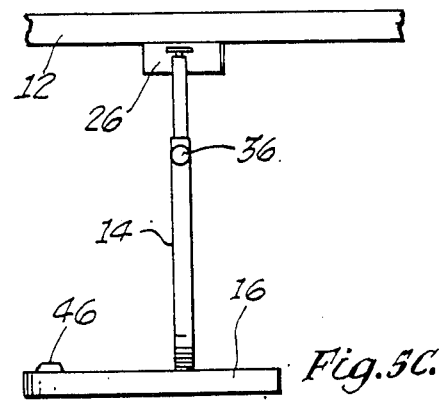
FIGS. 5A, 5B and 5C show various manners of using the system.
Figures 5A, 5B:
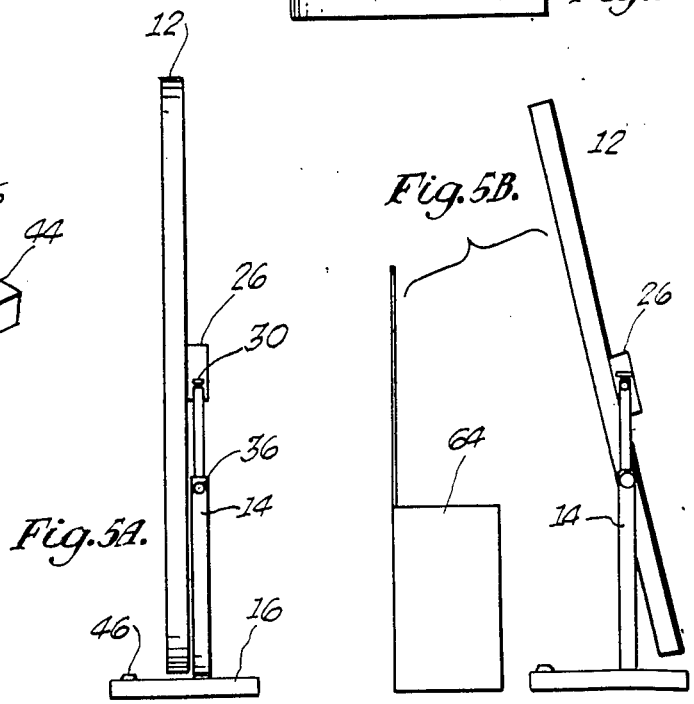

Referring to FIGS. 5A, 5B and 5C, various uses of system 10 are shown. In FIG. 5A a user can stand in front of the unit when canopy 12 is in a vertical position. In FIG. 5B, the user can sit in chain 64 and slightly tilt the canopy 12 as shown. In FIG. 5C, the user may lie on a bed or cot and rotate canopy 12 to the horizontal position. At the same time upper portion 32 of frame 16 can be raised.

What is claimed is:

1. A portable tanning system for providing tanning rays towards a user comprising:
    a canopy for holding a plurality of bulbs of a type providing ultraviolet light, said canopy having a wire receptacle for receiving wires and a path therein for coupling said received wires to said bulbs, said canopy having an open front end and a heat pervious material covering said back;
    a base, including at least one ballast for said bulbs and means to connect said ballast to a source of household current, said base also including a wire outlet, said base further including feet means thereunder positioned to allow said base to be freestanding at an angle other than vertical with respect to the ground; and
    connecting means of a hollow lightweight material connected to said base for connecting said canopy wire receptacle to said base wire outlet and, when in an operating position, for holding said base in a vertical position with respect to the ground and for holding said canopy in an adjustable position to provide said tanning rays towards said user.

2. The invention according to claim 1 wherein said connecting means is rotatable and vertically adjustable.

3. The invention according to claim 2 wherein said connecting means is pivotably connected to said canopy to allow said canopy to rotate with respect to said base.

4. The invention according to claim 3 wherein said canopy can rotate in one direction between the horizontal and the vertical positions.

5. The invention according to claim 4 wherein said base and connecting means constitutes at least sixty percent of the weight of said entire unit.

6. The invention according to claim 5 wherein said base further includes a timer.

7. The invention according to claim 6 wherein said feet means includes casters.

8. The invention according to claim 7 wherein said heat pervious material is a plastic sunscreen.

9. The invention according to claim 8 wherein said canopy is fabricated of high strength molded plastic.

10. The invention according to claim 9 wherein said canopy includes bulb holders coupled in circuit with said wires from said ballast and further includes integral supports to hold said bulbs separate from said bulb holders.

11. The invention according to claim 9 wherein said bulbs are held recessed within said canopy.

12. The invention according to claim 1 wherein said connecting means includes means for attaching said connecting means to said base to allow said connecting means to rotate about said means for attaching between a storage position and said operating position.

13. The invention according to claim 12:
    wherein said feet means include a pair of casters; and
    wherein said connecting means includes a third caster positioned at the end thereof remote from said means for attaching to triangularily support said tanning system in a vertical position by said three casters when said connecting means is rotated to said operating position and to support said system in a nonvertical position when said connecting means is rotated to said storage position.

14. The invention according to claim 12 wherein said base and connecting means constitutes at least sixty percent of the weight of said unit.

15. The invention according to claim 14 wherein said canopy constitutes less than thirty percent of the weight of said system.

16. The invention according to claim 15 wherein said base constitutes less than twenty percent of the volume of said system.

17. The invention according to claim 16 wherein said base further includes a timer.

18. The invention according to claim 17 wherein said base further includes casters.

19. The invention according to claim 16 wherein said base constitutes less than twenty prcent of the volume of said system.

20. The invention according to claim 19:
wherein said feet means include a pair of casters; and wherein said connecting means includes a third caster positioned at the end thereof remote from said means for attaching to triangularily support said tanning system in a vertical position by said three casters when said connecting means is rotated to said operating position and to support said system in a nonvertical position when said connecting means is rotated to said storage position.

21. The invention according to claim 1 wherein said heat pervious material is a plastic sunscreen.

22. The invention according to claim 1 wherein said canopy is fabricated of high strength molded plastic.

23. The invention according to claim 22 wherein said canopy includes bulb holders coupled in circuit with said wires from said ballast and further includes integral supports to hold said bulbs separate from said bulb holders.

24. The invention according to claim 23 wherein said bulbs are held recessed within said canopy.

* * * * *